United States Patent [19]

Asinger et al.

[11] 4,061,674

[45] * Dec. 6, 1977

[54] PROCESS OF MAKING PENICILLAMINE

[75] Inventors: Friedrich Asinger, Rott; Wolf-Dieter Pfeifer; Heribert Offermanns, both of Grossauheim; Paul Scherberich, Neu Isenburg; Gerd Schreyer, Grossauheim, all of Germany

[73] Assignee: Deutsche Gold- und Silber-Scheideanstalt vormals Roessler, Frankfurt, Germany

[*] Notice: The portion of the term of this patent subsequent to Mar. 23, 1993, has been disclaimed.

[21] Appl. No.: 657,605

[22] Filed: Feb. 12, 1976

Related U.S. Application Data

[63] Continuation of Ser. No. 317,403, Dec. 21, 1972, Pat. No. 3,946,069.

[30] Foreign Application Priority Data

Dec. 22, 1971 Germany .......................... 2163810

[51] Int. Cl.$^2$ .............................................. C07C 99/00
[52] U.S. Cl. .............................................. 260/534 S
[58] Field of Search ................................... 260/534 S

[56] References Cited

U.S. PATENT DOCUMENTS 3,946,069    3/1976    Asinger et al. ................ 260/534 S Primary Examiner—Joseph E. Evans
Attorney, Agent, or Firm—Cushman, Darby & Cushman

[57] ABSTRACT

Penicillamine or a homolog thereof is obtained by reacting a 2-disubstituted-5,5-alkyl-thiazolidine nitrile, alkyl having 1 to 6 carbon atoms, with a mineral acid in a two-stage proceeding wherein in the first stage relatively low temperatures and a relatively high concentration of the mineral acid are employed while in the second stage the concentration of the acid is relatively low and the temperatures are relatively high, the term "relatively" referring to the relationship of said two stages of the reaction with mineral acid.

7 Claims, No Drawings

PROCESS OF MAKING PENICILLAMINE

This is a continuation of application Ser. No. 317,403, filed Dec. 21, 1974, now U.S. Pat. No. 3,946,069.

BACKGROUND OF THE INVENTION

Penicillamine has already been made from 2,2,5,5-tetramethyl-thiazolidine-4-carbonitrile by converting the nitrile either directly or via the intermediate of the carbonamide into a tetramethyl-thiazolidine-4-carboxylic acid ester. The ester is then reacted with hydrochloric acid to form the hydrochloric acid salt of penicillamine and the penicillamine hydrochloride can then be neutralized with alkali to obtain the free acid (see Jahrbuch 1967 des Landesamtes fur Forschung Nordrhein-Westfalen, pages 11 to 35). This process however is complicated and expensive since it is necessary first to obtain the intermediate product, the carboxylic acid ester. Besides it results in only low yields. The direct conversion of the tetramethyl-thiazolidine-4-carbonitrile into a salt of penicillamine has not been possible heretofore.

It is therefore an object of the present invention to obtain penicillamine or a homolog thereof directly from a 2-disubstituted 5,5-dialkyl-thiazolidine-4-carbonitrile.

SUMMARY OF THE INVENTION

According to the invention a compound of the formula

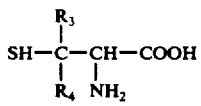

wherein $R_3$ and $R_4$ are as stated in the claims, that is penicillamine or a homologue thereof, is obtained by carrying out the reaction of the 2-disubstituted 5,5-dialkyl-thiazolidine-4-carbonitrile with mineral acid in two stages. In the first stage the mineral acid is employed in a relatively high concentration and the temperature is relatively low and in the second stage the concentration of the mineral acid is low relative to the first stage and the temperature is high relative to the first stage. In this manner the salts of penicillamine or its homologs are directly obtained from the nitriles at fairly high yields.

DETAILS OF THE INVENTION AND PREFERRED EMBODIMENTS

The starting products for the process of the invention are the 2-disubstituted 5,5-dialkyl-thiazolidine-4-carbonitriles of the general formula

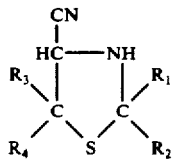

wherein $R_1$, $R_2$, $R_3$ and $R_4$ are the same or different. $R_1$ and $R_2$ may be alkyl, preferably of 1 to 6 carbon atoms which may also form a closed ring, alkenyl, preferably of 2 to 4 carbon atoms or alkaryl, preferably having 1 to 2 carbon atoms in the alkyl portion. $R_3$ and $R_4$ should be alkyl, preferably of 1 to 6 carbon atoms which may form a closed ring.

The process is of particular use for making penicillamine, which is also known as 2-amino-3-mercapto-isovalerianic acid. As starting products there are preferred the 2,2-dimethyl-, 2,2-diethyl- and 2-methyl-2-ethyl-5,5-dimethyl-thiazolidine-4-carbonitriles.

Penicillamine is used as an additive to feeds particularly for chicks or young pigs and as a pharmaceutical, for instance in the treatment of Wilson's disease or of cystinuria. Recently it has also come into wide use in the treatment of rheumatoid arthritis.

The 2-disubstituted starting product in the form of the 2-disubstituted-5,5-dialkyl-thiazolidine-4-carbonitrile can be obtained in known manner from the corresponding thiazoline-$\Delta^3$.

In order to make the nitriles the thiazolines are reacted at a low temperature with hydrogen cyanide. This reaction is preferably carried out in organic solvents, particularly alkanols such as methanol, or ethers such as diethyl ether or in aliphatic or aromatic hydrocarbons which may be substituted by halogen. The crude nitrile which is obtained from the reaction mixture by evaporation of the solvent, by cooling or by precipitation of the salts by means of acids, can be readily subjected to the reaction of the present invention.

This reaction involves the direct conversion of the nitrile into penicillamine or a homolog thereof. The reaction in general is carried out in the presence of at least a stoichiometric amount of water, relative to the nitrile, by reaction with a strong mineral acid. Suitable mineral acids are for instance sulfuric acid, hydrogen halide acids and mixtures thereof. Preferably the acid is hydrochloric acid. The reaction is preferably carried out upon exclusion of oxygen.

The acid concentration used in the reaction and the acid amounts and the temperatures as well as the reaction time are interdependent to a certain extent and also depend on the type of acid. Generally it is preferred to use temperatures of about 20° to 80° C, particularly below 80° C, in the first stage and acid concentrations of about 30 to 80 particularly in excess of 30, weight percent. In the second stage the temperatures should be from about 80° to 120° C, particularly in excess of 80° C, and the acid concentration should be from 10 to 30, particularly below 30 percent by weight.

It is preferred to carry out the reaction in hydrogen chloride. In this case the nitriles are preferably first reacted with hydrogen chloride of a concentration of at least 30 weight percent, particularly in excess of that amount, and preferably with concentrated hydrochloric acid for a time between 2 and 8 hours, and preferably from 2 to 4 hours at a temperature of about 20° to 80° C, particularly below 80° C and preferably between 45° and 55° C. In the second stage the reaction is carried out with hydrogen chloride of a concentration between 10 and 30 weight percent, particularly below 30 weight percent and preferably in an azeotropic mixture of hydrogen chloride with water for about 2 to 8, preferably 2 to 4 hours at a temperature between 80° and 110° C, particularly in excess of 80° C, preferably at a temperature between 100° and 110° C. It is generally preferred to start the first stage reaction at about 20° C and gradually increase the temperature slowly. Preferably there are used in the first stage at least 200 ml, preferably between 500 and 1000 ml hydrochloric acid per mol of nitrile. The transition from the higher to the lower acid concentration is effected by diluting the reaction mass with corresponding amounts of water, if desired in several batches, or by driving off a corresponding amount of hydrogen chloride.

The penicillamine or its homologs are then obtained from the reaction mixture which contains the corresponding compound as a salt of the mineral acid, by evaporation to dryness and extracting the residue with an alkanol, preferably with anhydrous methanol or ethanol. The free penicillamine or a homolog thereof is then precipitated from the extract by neutralization with alkali, preferably with an organic base such as triethylamine.

The following examples will further illustrate the invention.

EXAMPLE 1

145 g (1 mol) of 2,2,5,5-tetramethyl-thiazoline-$\Delta^3$ were dissolved in 300 ml methanol. The solution was reacted at 5° to 10° C with 30 g (1.1 mol) of liquid hydrogen cyanide and maintained for 60 minutes at a temperature between 10° and 30° C. The methanol was then distilled off.

The crude nitrile thus obtained was reacted upon cooling with 500 ml of concentrated hydrochloric acid. The mixture was maintained for 4 hours at 50° C and after adding 1,000 ml of water was kept for 4 hours under refluxing at boiling temperature (about 105° C). The reaction was carried out under an atmosphere of nitrogen. Thereafter followed evaporation to dryness whereupon the residue was extracted with anhydrous ethanol. The alcohol was then evaporated from the alcoholic solution. There remained penicillamine hydrochloride which had a melting point between 144° and 145° C. The yield was 149 g corresponding to 80% relative to the employed thiazoline.

The penicillamine hydrochloride was then dissolved in 500 ml of a 96% ethanol. By adding a solution of triethylamine in ethanol the pH was adjusted to 6.5. After a short time penicillamine precipitated. It had a melting point of 204° to 205° C. The yield was 105 g corresponding to 72% relative to the employed thiazoline.

EXAMPLE 2

This example generally followed the process described in Example 1. However, for a starting compound there were used 170 g (1 mol) of 2,2-diethyl-5,5-dimethylthiazoline-(3). The crude nitrile was reacted with 1000 ml of concentrated hydrochloric acid. The mixture was maintained for 5 hours at a temperature of 50° C in an atmosphere of nitrogen. Thereafter the temperature was increased and hydrogen chloride was driven off until the acid had the composition of the azeotropic mixture. The mixture was then maintained for 4 hours under refluxing at boiling point (about 105° C).

The further process was as in Example 1. The yield of penicillamine was 100 g corresponding to 68% relative to the employed thiazoline. The penicillamine had a melting point of 205° to 206° C.

EXAMPLE 3

The same process was used as in Example 2. However the starting product were 157 g (1 mol) 2-methyl-2-ethyl-5,5-dimethyl-thiazoline-(3). The yield of penicillamine was 110 g corresponding to 75% relative to the thiazoline starting product. The penicillamine had a melting point of 204° to 205° C.

EXAMPLE 4

183 g (1 mol) of 2,2-dimethyl-5,5-pentamethylene-thiazoline-(3) were dissolved in 300 ml methanol. The solution was reacted at 5° to 10° C with 30 g (1.1 mol) of liquid hydrogen cyanide. The mixture was then maintained for 60 minutes at a temperature of 10° to 30° C and thereafter treated with a stream of dry hydrogen chloride. There were obtained 210 g of thiazolidine-4-carbonitrile-hydrochloride corresponding to an 85% yield.

The thiazolidine-4-carbonitrile-hydrochloride was then first maintained for 8 hours in 1000 ml of concentrated hydrochloric acid under an atmosphere of nitrogen at a temperature of 45° to 50° C. After dilution with 1000 ml water the mixture was then maintained for 8 hours at boiling temperature. The mixture was finally cooled, filtered and evaporated to dryness under reduced pressure. The residue was extracted with methanol followed by evaporation of the extract. There were obtained 160 g of 2-amino-3-mercapto-3,3-pentamethylene-propionic acid-hydrochloride corresponding to a yield of 71% relative to the thiazoline starting product. The melting point of the compound was 218° C.

The obtained 2-amino-3-mercapto-3,3-pentamethylenepropionic acid-hydrochloride was dissolved in 600 ml of 98% methanol and adjusted to a pH between 5 and 6 with a solution of triethylamine in 98% methanol. The free 2-amino-3-mercapto-3,3-pentamethylene-propionic acid thus precipitated. It had a melting point of 210° to 212° C. The yield was 140 g corresponding to 62% relative to the thiazoline starting product.

EXAMPLE 5

The same process was used as in Example 4 but the starting product were 211 g (1 mol) of 2,2-diethyl-5,5-pentamethylene-thiazoline-(3). The thiazolidine-4-carbonitrile-hydrochloride was maintained in 1000 ml of concentrated hydrochloric acid for 8 hours at a temperature between 45° and 50° C. Thereafter the temperature was increased and hydrogen chloride was driven off for so long as to obtain an acid which had the composition of the azeotropic mixture. This mixture was then maintained for 8 hours under reflux at boiling temperature.

The further processing was as in Example 4. The yield of 2-amino-3-mercapto-3,3-pentamethylene-propionic acid was 145 g corresponding to a yield of 64% calculated on the thiazoline starting product. The compound had a melting point of between 210° and 211° C.

Without further analysis, the foregoing will so fully reveal the gist of the present invention that others can by applying current knowledge readily adapt it for various applications without omitting features that, from the standpoint of prior art, fairly constitute essential characteristics of the generic or specific aspects of this invention and, therefore, such adaptations should and are intended to be comprehended within the meaning and range of equivalence of the following claims.

What is claimed as new and desired to be protected by Letters Patent is set forth in the appended claims:

1. A process for the production of a compound having the formula

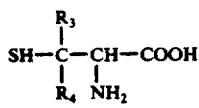

I wherein:
R₃ and R₄ are each alkyl of 1 to 6 carbon atoms or which together form a closed ring, which process comprises heating in two stages in the presence of at least a stoichiometric amount of water and hydrochloric acid a thiazolidine-4-carbonitrile having the formula:

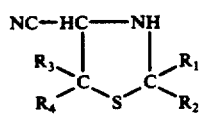

II wherein:
R₃ and R₄ have the meaning as above, and
R₁ and R₂ are each alkyl of 1 to 6 carbon atoms or which together form a closed ring, or are alkenyl of 2–4 carbon atoms or alkyl-substituted aryl, the alkyl substituent having a total of 1–2 carbon atoms,
the heating in the first stage being conducted at a temperature between 20° and 80° C in hydrochloric acid having a concentration of at least 30% by weight of hydrogen chloride, and the heating in the second stage being conducted at a temperature between 80° and 110° C in hydrochloric acid having a concentration of at least 10 and at most 30% by weight of hydrogen chloride and extracting the compound above I or its hydrochloride from the mixture.

2. A process as defined in claim 1 in which the thiazolidine-4-carbonitrile is the 4-carbonitrile of 2,2-dimethyl-5,5-pentamethylenethiazolidine or 2,2-diethyl-5,5-pentamethylenethiazolidine.

3. The process of claim 1, wherein the thiazolidine used as starting compound is obtained by reacting the corresponding thiazoline-Δ³ with hydrogen cyanide.

4. A process as defined in claim 1 in which the heating in each of the two stages is conducted for a period between 2 and 8 hours.

5. A process as defined in claim 1 in which the heating in the first stage is commenced at a temperature of 20° C and the temperature is then gradually raised to a desired maximum temperature.

6. A process as defined in claim 1 in which the heating with hydrochloric acid is conducted in the absence of oxygen.

7. A process as defined in claim 1 in which the concentration of hydrochloric acid in the reaction mixture at the end of the first stage of heating is adjusted to that specified for the second stage by addition of water to the said reaction mixture or by evaporating off a portion of the hydrochloric acid in the said reaction mixture.

* * * * *